United States Patent [19]
Hirschberg et al.

[11] Patent Number: 5,235,978
[45] Date of Patent: Aug. 17, 1993

[54] IMPLANTABLE ARRANGEMENT FOR THE DEFIBRILLATION OR CARDIOVERSION OF A HEART

[75] Inventors: Jakub Hirschberg, Taeby; Olof Stegfeldt, Alta; Lars-Olof Peterson, Bromma; Malin Alm, Solna, all of Sweden

[73] Assignee: Siemens Aktiengesellschaft, Munich, Fed. Rep. of Germany

[21] Appl. No.: 895,859

[22] Filed: Jun. 9, 1992

[30] Foreign Application Priority Data

Mar. 10, 1992 [SE] Sweden ............... 92104097-8

[51] Int. Cl.⁵ .................................. A61N 1/365
[52] U.S. Cl. ................................ 607/5; 607/119
[58] Field of Search .......... 128/419 D, 419 G, 419 P, 128/785, 786

[56] References Cited

U.S. PATENT DOCUMENTS

| | | | |
|---|---|---|---|
| 4,154,247 | 5/1979 | O'Neill | 128/419 P |
| 4,414,986 | 11/1983 | Dickhudt et al. | 128/785 |
| 4,662,377 | 5/1987 | Heilman et al. | 128/419 D |
| 4,708,145 | 11/1987 | Tacker, Jr. et al. | 128/419 D |
| 4,722,353 | 2/1988 | Sluetz | 128/419 P |
| 4,727,877 | 3/1988 | Kallok | 128/419 D |
| 4,991,603 | 2/1991 | Cohen et al. | 128/419 D |
| 5,105,810 | 4/1992 | Collins et al. | 128/419 PG |

FOREIGN PATENT DOCUMENTS

| | | | |
|---|---|---|---|
| 0057448 | 8/1982 | European Pat. Off. | 128/419 P |
| 0030953 | 9/1984 | European Pat. Off. | 128/419 D |
| 0281219 | 9/1988 | European Pat. Off. | 128/419 D |
| 0373953 | 6/1990 | European Pat. Off. | 128/419 D |
| 3919498 | 1/1990 | Fed. Rep. of Germany | 128/419 D |
| 2157178 | 10/1985 | United Kingdom | 128/419 D |

Primary Examiner—Kyle L. Howell
Assistant Examiner—George Manuel
Attorney, Agent, or Firm—Hill, Steadman & Simpson

[57] ABSTRACT

An implantable arrangement for effecting in vivo defibrillation or cardioversion of a heart has a first electrode disposed in the inferior vena cava, a second electrode disposed in the right ventricle, and a planar electrode disposed outside of the heart. Pulse generating means are provided which simultaneously charge all three electrodes with pulses. An optimally low energy for successfully achieving defibrillation is thereby achieved.

15 Claims, 2 Drawing Sheets

IMPLANTABLE ARRANGEMENT FOR THE DEFIBRILLATION OR CARDIOVERSION OF A HEART

BACKGROUND OF THE INVENTION

1. Field of the Invention

The present invention is directed to an implantable arrangement for defibrillation or cardioversion of a heart.

2. Related Application

The subject matter of the present application is related to that of application Ser. No. 07/895,810, filed simultaneously herewith, of the same inventors and assigned to the same Assignee as the present application.

3. Description of the Prior Art

An implantable system for in vivo defibrillation or cardioversion of a heart is disclosed in U.S. Pat. No. 4,662,377. This known system includes two intravascular electrodes, which are both carried on a catheter which is introduced into the right half of the heart. The intravascular electrodes are spaced from each other along the cathode so that when the cathode is properly in place within the heart, one electrode is disposed in the right ventricle of the heart and the other electrode is disposed in the superior vena cava. A planar electrode is disposed outside of the heart, opposite the left ventricle and is subcutaneously implanted at that location. The planar electrode is connected to the electrode in the superior vena cava and is connected to an output terminal of an implantable defibrillation pulse generator. The other output terminal of the pulse generator is connected to the electrode disposed in the ventricle so that, when defibrillating the heart, the current surge is divided into a first sub-current between the electrode in the ventricle and the electrode in the superior vena cava, and a second sub-current between the electrode in the ventricle and the planar electrode.

Another arrangement for defibrillation or cardioversion of a heart is disclosed in U.S. Pat. No. 4,708,145 which also uses a catheter having an electrode disposed in the right ventricle and another electrode in the superior vena cava, and a planar electrode which can be either subcutaneously disposed or epicardially disposed in the proximity of the diaphragm. Defibrillation pulses are supplied sequentially between the electrode and the superior vena cava and the electrode in the ventricle, and the planar electrode and the electrode in the ventricle. Thus, only two electrodes simultaneously participate in the delivery of pulses, and a true distribution of the current density into different zones of the heart muscle therefore does not occur. As an alternative to the aforementioned electrode placement, the electrode in the superior vena cava may be disposed in the inferior vena cava. Another electrode arrangement is disclosed in this patent wherein only planar electrodes are arranged on the heart.

A defibrillation arrangement is disclosed in European Application 0 373 953 wherein, when employing three electrodes, one electrode is arranged in the right ventricle via a catheter, another electrode is arranged in the vena cordis magna (great coronary vein) via a further catheter, and a third planar electrode is subcutaneously arranged disposed opposite the left ventricle. Defibrillation pulses are supplied either between one of these electrodes and the two other electrodes, which are connected to each other to achieve this purpose, or alternatively the electrodes may be successively charged with a defibrillation pulse in pairs.

Lastly, German OS 39 19 498 discloses an implantable arrangement for defibrillation or cardioversion of a heart, wherein one of a plurality of electrodes is disposed in the right ventricle, and the other electrodes, which are planar electrodes, are placed outside the heart or implanted subcutaneously. Defibrillation pulses are supplied between the electrode in the ventricle and the outer electrodes, which are connected to each other, so that the electrical current density is divided according to the spatial arrangement of the electrodes, and thus tends to penetrate the thickest zones of the heart muscle. If the defibrillation energy is to be optimally exploited, it is then necessary that the outer electrodes be applied directly to the epicardium. This requires, however, surgical opening of the thorax.

SUMMARY OF THE INVENTION

It an object of the present invention to provide an arrangement for defibrillating a heart in which an optimally low value for the minimum defibrillation energy is achieved by means of a correspondingly optimum distribution of the current density in the heart muscle.

The above object is achieved in accordance with the principles of the present invention in an implantable defibrillation/cardioversion system having three electrodes, a first of which is disposed in the right ventricle via a catheter, a second of which is disposed in the inferior vena cava via a catheter (which may be the same catheter as is used for the ventricular electrode, or may be a different catheter), and a third of which is a planar electrode disposed outside of the heart. The three electrodes are simultaneously charged with defibrillation pulses.

In tests using such an arrangement, values for the defibrillation threshold, i.e., the minimally required defibrillation energy, were achieved which were no higher, and even partially lower, than for comparable arrangements using epicardial electrodes. Differing from these comparable arrangements, however, the tested arrangement employed a planar electrode which was subcutaneously arranged, so that it was not necessary to open the thorax. Although the use of an electrode disposed in the inferior vena cava, instead of in the superior vena cava, is described in the aforementioned U.S. Pat. No. 4,708,145, the delivery of the defibrillation pulses in the arrangement disclosed in that patent ensues at identical points in time only between two respective electrodes, so that the distribution of the current density over the heart muscle, as is accomplished in the subject matter of the present invention by the simultaneous charging of all three electrodes, is not achieved.

If the intravascular electrodes are to be introduced into the intravascular system via the inferior vena cava, the electrode in the ventricle and the electrode in the inferior vena cava are preferably carried on the same catheter. This achieves a precisely defined spacing between the two intravascular electrodes, and moreover permits the electrodes to be simultaneously positioned at the desired locations.

If positioning of the electrode arrangement is to be undertaken proceeding from the superior vena cava, the electrode in the inferior vena cava is preferably carried by a separate, second catheter. In order to achieve a stable positioning of the second catheter in its implanted, final position, the second catheter carrying the inferior vena cava electrode preferably includes means carried at the distal end region of the electrode for fixing the electrode in the inferior vena cava. Such fixing means may, for example, be in the form of spreader elements, or by providing the distal end of the electrode with a helical spring, both of which permit the distal end of the catheter to be immovably retained in the vein. It is also possible to anchor the distal end in the vein wall using hooks or helically shaped continuations of the electrode.

In a preferred embodiment of the invention, the second catheter, carrying the inferior vena cava electrode, carries means for fixing this catheter in the region of the right atrium. This prevents the second catheter from dislocating in the relatively large volume of the vein regions, and from potentially proceeding into the interior of the heart. The means for fixing the second catheter in the region of the right atrium are preferably in the form of a deformation of the catheter, departing from a straight-line course, or spreader elements projecting laterally from the catheter. The fixing means can be activated only when the catheter has been positioned in its final position. The deformation of the catheter deviating from a straight-line path can be accomplished by pre-bending the catheter at a predetermined location by means of a stylet or control wire guided in the interior of the catheter, with the catheter retaining the predetermined, pre-bent deformation after the removal of the control wire or stylet. A further possibility for deforming the catheter is to provide elements as a part of the catheter which consists of a so-called "shape memory" metal alloy, which assume a prescribed shape when a predetermined temperature level is reached, this temperature level, for this particular application, corresponding to body temperature.

In an advantageous embodiment of the invention which permits multiple use of the catheter, the means for fixing the second catheter may project into the region of the right atrium, and carry an atrial electrode which is connected to a detector and/or heart pacemaker circuit via an electrode line guided inside the catheter.

In the simplest case, two of the respective defibrillation electrodes, preferably the electrode in the inferior vena cava and the planar electrode, are electrically connected. This achieves the division, during defibrillation of the heart, of the current surge into two sub-currents, the two sub-currents respectively flowing between the remaining electrode and the two connected electrodes.

In another preferred embodiment of the invention, the pulse-generating means for simultaneously charging the three electrodes is a means for simultaneously charging the three with respectively different voltages. This permits the current distribution in the heart to be set not only in dependence on the spatial arrangement of the electrodes, but also by means of the different electrical voltages at the outputs of the pulse generator.

DESCRIPTION OF THE PREFERRED EMBODIMENTS

Figure 1:
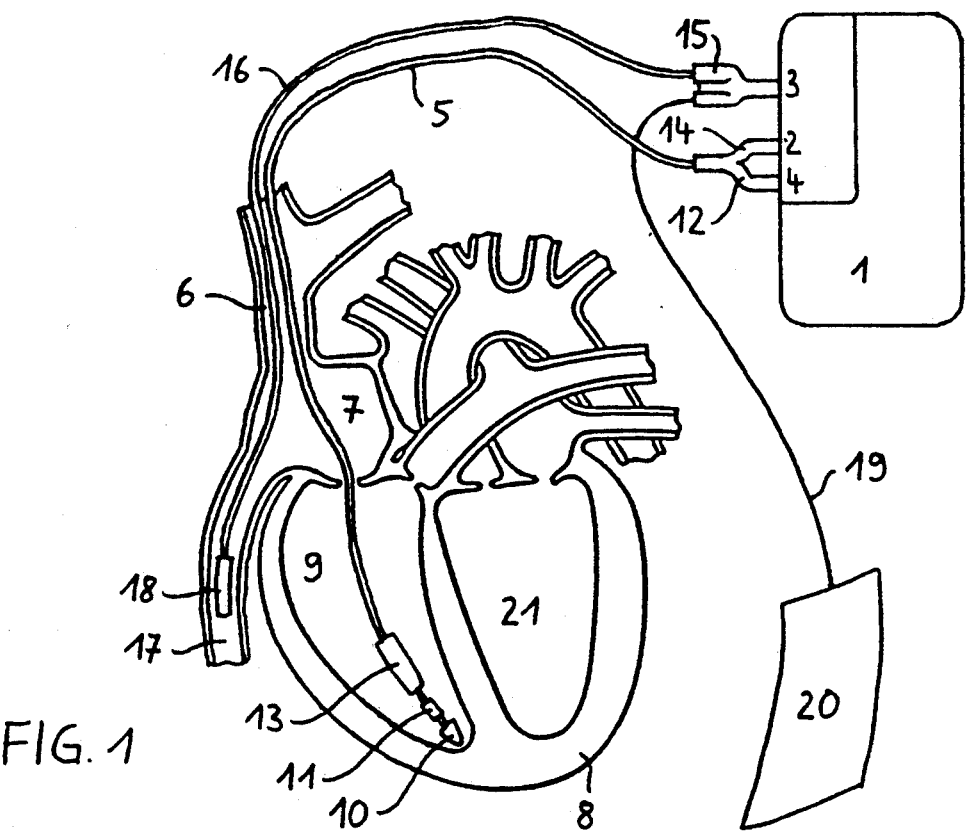
FIGS. 1 through 4 respectively show different exemplary embodiments of an arrangement for defibrillating and/or cardioverting a heart, constructed in accordance with the principles of the present invention.

An implantable defibrillator/cardioverter 1 is shown in FIG. 1, constructed in accordance with the principles of the present invention, having two output terminals 2 and 3 at which defibrillation pulses are supplied as an output, and having a further, bipolar terminal 4 which is connected to a detector and heart pacemaker circuit (not shown) in the interior of the defibrillator/cardioverter 1. A catheter 5 is connected to the output terminals 2 and 4, this catheter 5 being conducted through the superior vena cava and the right atrium 7 of a heart 8 into the right ventricle 9. The catheter 5 has a distal end with a tip electrode 10 and a ring electrode 11, the ring electrode 11 being spaced from the tip electrode 10 in the proximal direction. Both the tip electrode 10 and the ring electrode 11 are connected to bipolar terminal 4 of the defibrillator/cardioverter 1 via electrode lines (not shown) in the inside of the catheter 5. These lines are respectively separated in a first branching 12 at the proximal end of the catheter 5. The tip electrode 10 and the ring electrode 11 are used for the detection of cardiac activity and/or the delivery of pacing pulses.

The catheter 5 further carries a defibrillation electrode 13, which is disposed in the right ventricle 9 and is connected to the output terminal 2 of the defibrillator/cardioverter 1 via a line (not shown) in the inside of the catheter 5. This line is connected to the defibrillator/cardioverter 1 via a branching 14 at its proximal end. An adaptor piece 15 is inserted in the second output terminal 3 of the defibrillator/cardioverter 1, and is connected to a second defibrillation electrode 18 positioned in the inferior vena cava 17 via a second catheter 16. The second output terminal 3 is also connected to a planar electrode 20 via an insulated line 19. The planar electrode 20 is subcutaneously implanted in the region of the left ventricle 21 of the heart 8, or at a distance from the heart 8. In the exemplary embodiment shown in FIG. 1, defibrillation of the heart 8 ensues respectively between the electrode 13 in the right ventricle 9 and the electrode 18 in the inferior vena cava and the electrode 20 at the outside of the heart 8, which are electrically connected to each other. The minimum defibrillation energy required for this purpose exhibits values which are no higher than and partially even lower than, the defibrillation energy required in comparable arrangements having epicardial electrodes.

Figure 2:
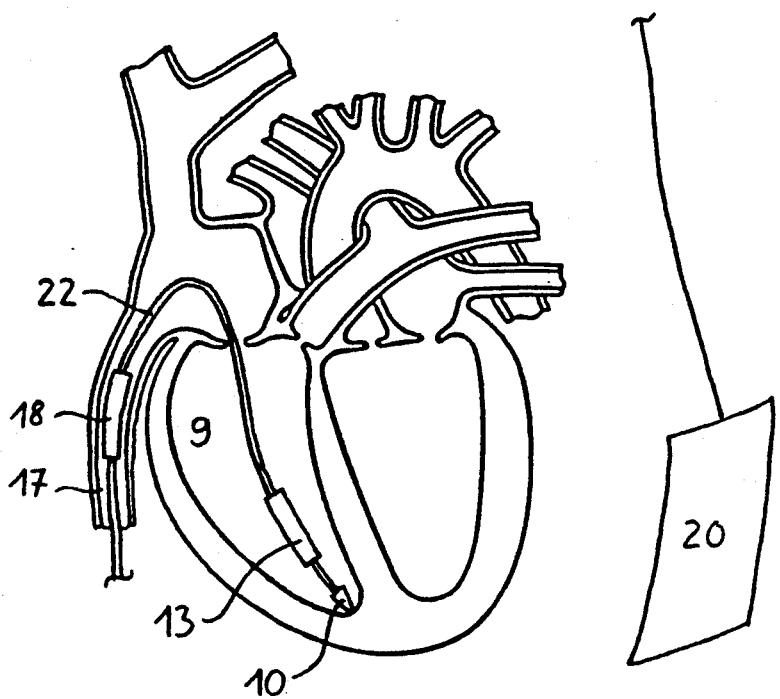

The exemplary embodiment of the invention shown in FIG. 2 differs from the embodiment of FIG. 1 in that the defibrillation electrode 13 in the right ventricle 9 and the electrode 18 in the inferior vena cava 17 are arranged on a common catheter 22, which is introduced into the intravascular system through the inferior vena cava 17. Moreover, the defibrillation electrode 13 in the ventricle 9 in the embodiment of FIG. 2 serves as the return electrode for the tip electrode 10, and therefore the catheter 22 does not have a ring electrode.

Figure 3:
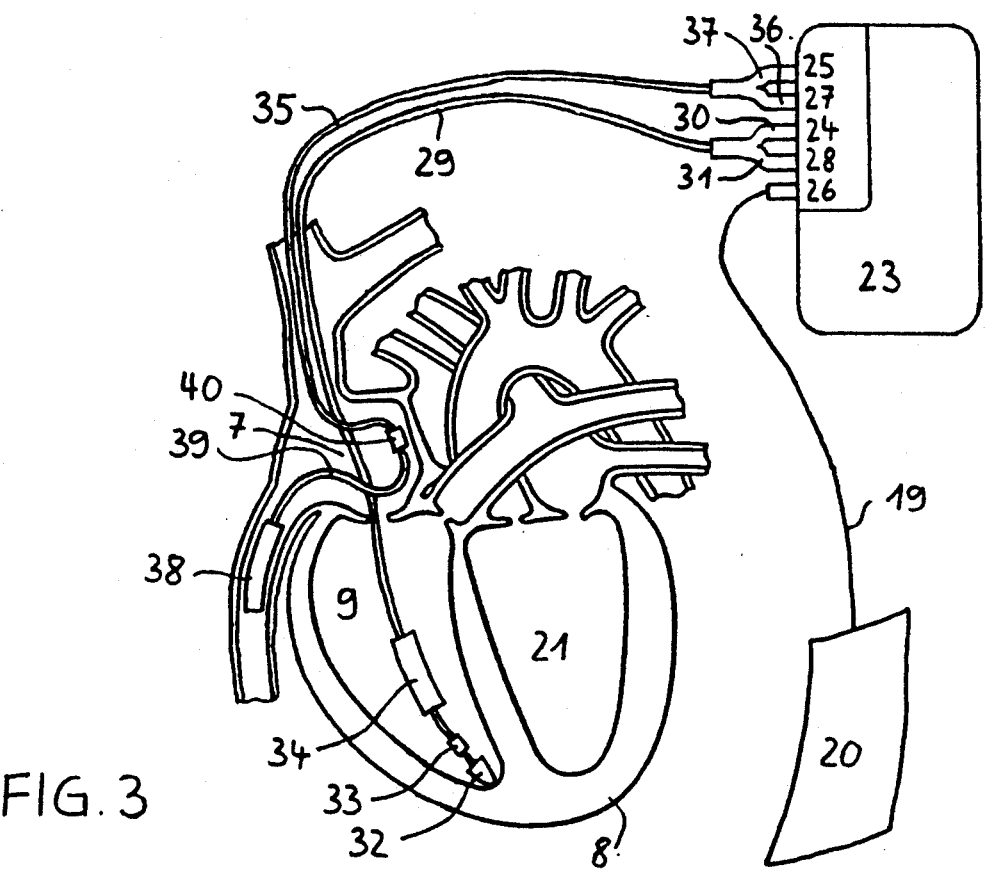

An implantable defibrillator/cardioverter 23 is shown in the embodiment of FIG. 3 having three output terminals 24, 25 and 26 for supplying defibrillation pulses, and a further, unipolar terminal 27 and a bipolar terminal 28 which are both connected to a detector and heart pacemaker circuit (not shown) in the inside of the defibrillator/cardioverter 23. A first catheter 29 has a proximal end with branches 30 and 31 respectively connected to the terminals 24 and 28 of the defibrillator/cardioverter 23. The catheter 29 is conducted through the superior vena cava 6 and the right atrium 7 of the heart 8 into the right ventricle 9, and has a distal end located in the right atrium 7 having a tip electrode 32 and a ring 33 spaced therefrom in the proximal direction. Both of these electrodes are connected to the detector and heart pacemaker circuit in the defibrillator/cardioverter 23 via electrode lines (not shown) in the inside of the catheter 29 and via the bipolar terminal 28.

The catheter 29 also has a defibrillation electrode 34 disposed in the ventricle 9, which is connected to the terminal 24 of the defibrillator/cardioverter 23 via a line (not shown) in the inside of the catheter 29.

A further catheter 35 is connected to the terminals 25 and 27 via respective branches 36 and 37 at its proximal end. At its distal end, the second catheter 35 carries a defibrillation electrode 38, which is positioned in the inferior vena cava 17 and which is connected to the terminal 25 of the defibrillator/cardioverter 23 via a line (not shown) in the inside of the catheter 35. In the region between the superior vena cava 6 and the inferior vena cava 17, the second catheter 35 has a deformation 39 which deviates from a straight-line path. The deformation 39 of the catheter 35 extends into the atrium 7 of the heart 8, at which location an atrial electrode 40 is disposed. The atrial electrode 40 is connected to the detector and/or heart pacemaker circuit of the defibrillator/cardioverter 23 via an electrode line (not shown) inside the catheter 35 and via the unipolar terminal 27.

A planar electrode 20 is connected to the third defibrillation terminal 26 via an insulated electrical line 19. The planar electrode 20 is subcutaneously disposed lying opposite the left ventricle 21 of the heart 8.

Instead of the atrial electrode 40, a measuring probe for measuring pressure, flow, temperature or gas saturation of the venous blood may be used at that location.

For defibrillating the heart 8, the defibrillator/cardioverter 23 generates different voltages between its output terminals 24, 25 and 26, as a result of which a current distribution in the heart 8 is achieved which is dependent not only on the spatial arrangement of the electrodes 20, 34 and 38, but which also may be additionally set by means of the different voltages between the electrodes 20, 34 and 38.

Figure 4:
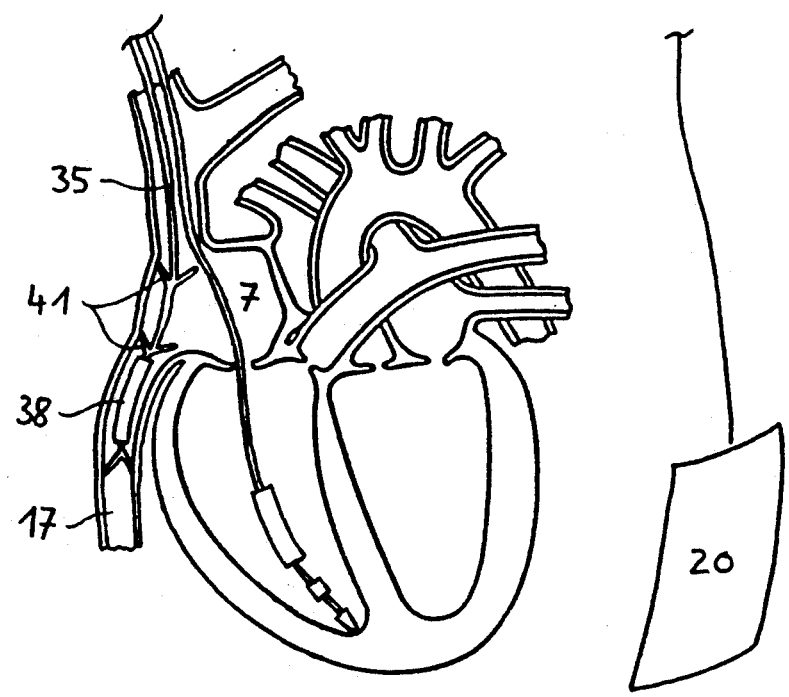

The exemplary embodiment of the invention shown in FIG. 4 has a second catheter 35 with spreader elements 41 for fixing the position of the catheter 35. The spreader elements 41 are disposed in the region of the atrium 7 as well as in the region of the electrode 38 in the inferior vena cava 17. These spreader elements can be activated after the second catheter 35 has been inserted to its desired position, so that the catheter 35 is anchored and the position of the electrode 38 is thereby fixed.

Although modifications and changes may be suggested by those skilled in the art, it is the intention of the inventors to embody within the patent warranted hereon all changes and modifications as reasonably and properly come within the scope of their contribution to the art.

We claim as our invention:

1. An implantable defibrillation/cardioversion system comprising:
   a first electrode means for positioning in the right ventricle of a heart;
   a second electrode means for positioning in the inferior vena cava;
   a planar third electrode means for positioning outside said heart in the region of the left ventricle;
   conductor means for supplying electrical energy to said planar third electrode means;
   catheter means for supplying electrical energy to said first and second electrode means; and
   pulse generator means, for in vivo implantation and being electrically connected to said catheter means and to said conductor means, for generating defibrillation/cardioversion pulses for simultaneously charging said first, second and third electrode means for electrically stimulating said heart.

2. A system as claimed in claim 1 wherein said catheter means comprises a single catheter carrying both said first and second electrode means.

3. A system as claimed in claim 1 wherein said catheter means comprises a first catheter carrying said first electrode means and a second, separate catheter carrying said second electrode means.

4. A system as claimed in claim 3 further comprising means disposed at a distal end region of said second catheter for fixing said second electrode in the inferior vena cava.

5. A system as claimed in claim 4 wherein said means for fixing is a means for positioning in the right atrium of said heart for fixing a portion of said second catheter in the right atrium.

6. A system as claimed in claim 5 wherein said second catheter has a deformation deviating from a straight-line path for fixing the second catheter.

7. A system as claimed in claim 5 wherein said means for fixing the second catheter consists of a plurality of spreader elements laterally projecting from said second catheter.

8. A system as claimed in claim 5 further comprising an atrial electrode means connected to said second catheter positioned and at said portion of said second catheter for fixing in said right atrium and wherein said pulse generator means includes at least one of a means for detecting cardiac activity and means for generating cardiac pacing pulses electrically connected to said atrial electrode means via said second catheter.

9. A system as claimed in claim 1 further comprising means for electrically connecting two of said electrode means.

10. A system as claimed in claim 9 wherein said means for electrically connecting two of said electrode means is a means for electrically connecting said second electrode and said planar third electrode.

11. A system as claimed in claim 1 wherein said pulse generator means is a means for simultaneously charging said first, second and third electrode means with respectively different voltages.

12. An implantable defibrillation/cardioversion system comprising:
    three electrodes for delivering electrical energy to a heart, including a first electrode means for positioning in the inferior vena cava;
    pulse generator means for generating stimulation pulses for delivery to said three electrodes for stimulating said heart; and
    means electrically connecting said three electrodes to said pulse generator means including a first catheter carrying said first electrode means at a free end thereof for extending through the superior vena cava into the inferior vena cava.

13. A system as claimed in claim 12 wherein a second electrode means of said three electrodes is for positioning in the right ventricle of said heart, and further comprising a second catheter carrying said second electrode means for extending from said pulse generator means through the superior vena cava into the right ventricle.

14. A system as claimed in claim 13 wherein a third electrode means of said three electrodes is for positioning outside of said heart in the region of the left ventricle.

15. A system as claimed in claim 12 wherein a second electrode means of said three electrodes is for positioning outside of said heart in the region of the left ventricle.

* * * * *

UNITED STATES PATENT AND TRADEMARK OFFICE
CERTIFICATE OF CORRECTION

PATENT NO. : 5,235,978
DATED : August 17, 1993
INVENTOR(S) : Hirschberg et al.

It is certified that error appears in the above-indentified patent and that said Letters Patent is hereby corrected as shown below:

On the title page, item [75] Inventors: please add --Staffan Bowald, Almunge, Sweden-- as a co-inventor.

Signed and Sealed this

Twenty-second Day of February, 1994

Attest:

BRUCE LEHMAN

*Attesting Officer*  *Commissioner of Patents and Trademarks*